US006893404B2

(12) United States Patent
Ragnarsdottir

(10) Patent No.: US 6,893,404 B2
(45) Date of Patent: May 17, 2005

(54) BREATHING MOVEMENT MEASUREMENTS AND APPARATUS

(75) Inventor: Maria Ragnarsdottir, Reykjavik (IS)

(73) Assignee: Remo Ehf, Reykjavik (IS)

( * ) Notice: Subject to any disclaimer, the term of this patent is extended or adjusted under 35 U.S.C. 154(b) by 61 days.

(21) Appl. No.: 10/240,828

(22) PCT Filed: Apr. 4, 2001

(86) PCT No.: PCT/IS01/00008

§ 371 (c)(1),
(2), (4) Date: Feb. 10, 2003

(87) PCT Pub. No.: WO01/76467

PCT Pub. Date: Oct. 18, 2001

(65) Prior Publication Data

US 2003/0220570 A1 Nov. 27, 2003

Related U.S. Application Data

(60) Provisional application No. 60/195,190, filed on Apr. 7, 2000.

(30) Foreign Application Priority Data

Apr. 7, 2000 (IS) .................................... 5432

(51) Int. Cl.$^7$ ................................. A61B 5/08
(52) U.S. Cl. ...................................... 600/534; 600/529
(58) Field of Search ............................. 600/534, 529, 600/300, 532–533, 535–538

(56) References Cited

U.S. PATENT DOCUMENTS

| 4,495,950 A | | 1/1985 | Schneider |
| 4,884,578 A | * | 12/1989 | Morgenstern ............... 600/483 |
| 5,577,502 A | | 11/1996 | Darrow et al. |
| 5,588,439 A | | 12/1996 | Hollub |

FOREIGN PATENT DOCUMENTS

| DE | 31 09 026 A | | 9/1982 | |
| EP | 0 919 184 A | | 6/1999 | |
| GB | 2192713 A | | 1/1988 | |
| RU | 2072232 C1 | * | 1/1997 | ............ A61B/5/08 |

OTHER PUBLICATIONS

Eskov et al, Jan. 27, 1997, Translation of Russian Patent No. 2072232 C1.*

* cited by examiner

*Primary Examiner*—Robert L. Nasser
*Assistant Examiner*—Navin Natnithithadha
(74) *Attorney, Agent, or Firm*—Birch, Stewart, Kolasch & Birch, LLP

(57) ABSTRACT

A method and apparatus for measuring breathing movements and determining breathing patterns, by measuring the simultaneous movement of a plurality of points of a human subject, such that a breathing pattern may be determined based on data obtained in a single acquisition. The method provides a symmetry breathing pattern parameter.

20 Claims, No Drawings

BREATHING MOVEMENT MEASUREMENTS AND APPARATUS

This application claims the benefit of Provisional Application No. 60/195,190 filed Apr. 7, 2000.

This application is the national phase under 35 U.S.C. §371 of PCT International Application No. PCT/IS01/00008 which has an International filing date of Apr. 4, 2001, which designated the United States of America.

FIELD OF THE INVENTION

The present invention is within the field of physical measurements of body functions, specifically measurements of breathing movements of the chest and abdomen.

TECHNICAL BACKGROUND AND PRIOR ART

Many medical and physical conditions will affect the proper functioning of the breathing organs. The effects may be directly related to the physical condition of the lungs themselves and/or the many correlated functions that provide the breathing movements controlling the inspiration and expiration of the lungs. Several diseases have an effect on breathing movements and breathing patterns such that, e.g., movements of either the upper or lower chest or abdomen are diminished, affecting the proper respiration and ventilation of the subject. After operations on the chest or upper abdominal area, such as heart or lung operations where the chest has to be opened, subjects commonly have post-operative breathing complications.

Methods of measuring breathing movements include measuring the circumference of the chest and abdomen with a common measuring tape during inspiration and expiration (in- and out-breathing), such a measurement will, however, not give a simultaneous measuring during the same breath at more than one location. It is also difficult to obtain reproducible and precise measurements of changes in the circumference.

Respitrace (™) is a device based on 'respiratory inductive pletysmography' and provides time-dependent circumference measurements at two different heights simultaneously (see, e.g., Verschakelen, J. A., Demets, M. G. *Am. J. Resp. Critical Care Med.* 151, 1995, 399–405). Two spirals are put around the subject and changes in the circumference change the length of the spirals and thus their electrical conductivity.

In studies with a magnetometer the change in diameter is measured at two points at the center of the subject, typically on the center of the sternum and on the abdomen (e.g., Sharp, J. T., et al. *J. App. Physiol.* 39, 1975, 608–618). Two pairs of electrical coils are placed in contact with the body of the subject such that one coil of each is in front of the body and the other is directly behind the body. An AC current is led to the posterior coils which induces an electromagnetic field between the posterior and anterior coils and a potential is measured in the anterior coils that changes as the distance between the coils changes with the breathing of the subject. None of the above methods will allow a detailed and well-resolved analysis of breathing movements, such as e.g. to obtain symmetry-resolved data.

The Elite system (see U.S. Pat. No. 4,706,296) used in a study by De Groote et al. (De Groote et al. *J. Appl. Physiol.* 83 (5): 1531–1537, 1997) measures chest wall motions by recording the position of markers placed on an object in motion by using television cameras that have different viewpoints. The system supplies the acquisition of two-dimensional frames for each camera and then computes 3D coordinates of each marker as a function of time. The system as described by De Groote et al. uses two television cameras, and the motion of different subsets of markers is determined by comparing image data from six successive acquisitions, where the orientation of the subject is changed relative to the cameras in between every two acquisitions.

No systems have however been suggested in the prior art, wherein breathing patterns are obtained by measuring the simultaneous movement of a plurality of points, wherein the movement is measured by the change in the distance from each point to a reference point, such that a breathing pattern may be obtained in a single acquisition.

In particular, no such methods have been suggested for measuring the symmetry of breathing movements, that is whether the left and right side of a subject show equal breathing movements or whether a particular breathing problem will affect one side of the body more than the other. This can be suspected, e.g., in many heart operations where the sternum is cleaved and the left side of the rib cage may be forced upwards 3.5–5.5 cm during the operation. No data however seems to be available in the medical literature, discussing or describing post-operative effects on breathing movements, after such invasive surgery, and indeed, the inventors are not aware of any data discussing symmetry/asymmetry of breathing and quantitative measurements thereof. Methods will therefore be appreciated, to monitor such post-operative conditions and other conditions which may affect breathing symmetry and other breathing parameters.

An earlier disclosure by the inventor outlines a possible setup for breathing movement measurements based on using distance sensors. (Ragnarsdóttir, *Icel. Med. J.* vol. 85, no. 4,1999, pp. 313–314.)

It has since been found that such an instrumental setup and other types of imaging devices can be used to determine breathing patterns which can be described by a novel set of breathing pattern parameters.

SUMMARY OF THE INVENTION

In a first aspect, the invention provides a method for measuring breathing movements comprising measuring the simultaneous movement of a plurality of points of a human body, wherein the movement is measured by the change in the distance from each point of the plurality of points to one or more reference points, wherein the movement is measured over a time period so as to determine a breathing pattern.

In a further aspect, the invention discloses methods for evaluating the effect of a medical condition on breathing functions by determining breathing patterns by use of the methods according to the invention.

In yet a further aspect, the invention provides an apparatus for determining breathing patterns of a human comprising an imaging device comprising one or more distance measurement devices that measure the change in distance from each point of a plurality of points to one or more reference points; for measuring the simultaneous movement of a plurality of points of a human body to obtain a breathing pattern.

In a still further aspect, a method is provided for determining breathing patterns comprising: providing a set of data for breathing movement measurements over a period of time; entering the data into a computer; calculating with a computer program breathing pattern parameters selected from the group comprising type of breathing, rhythm of breathing, magnitude of breathing movements, frequency of breathing movements, and symmetry of breathing movements.

DETAILED DESCRIPTION

The method according to the invention for determining breathing patterns comprises measuring the simultaneous movement of a plurality of points of a human body. Breathing patterns is a concept used to describe breathing in physical terms. There is however, no commonly accepted general definition of the term. The inventor has defined a set of parameters that are useful to describe breathing patterns as are obtainable with the methods of the invention. The parameters are the following: type of breathing, rhythm of breathing, magnitude of breathing movements, frequency of breathing movements, and symmetry of breathing movements. Type of breathing indicates whether the breathing movements are predominantly abdominal, low-costal or high-costal (upper costal), or other type. Rhythm of breathing is the time ratio between inspiration time and expiration time. Magnitude of breathing movements is the excursion of the diaphragm and ribs from FRC (functional residual capacity, i.e., the resting breathing position after expiration) to full inspiration in Vt (tidal volume, after resting inspiration) and VC (vital capacity, after maximum inspiration). Frequency of breathing movements is how often a person breathes in and out in a given period of time such as in one minute. Symmetry of breathing movements indicates whether the magnitude of breathing movements is the same on the left and right side of sternum.

An essential feature of the method of the invention is to provide simultaneous movement measurements of a plurality of points of a human subject. In this context the term simultaneous is to be understood such that a simultaneous measurement of the movement of two points will provide comparable movement profiles for these two points in the same breath (inspiration and expiration). Consequently, using a computer program that controls the collection of measurement data through an electronic circuit, from a number of points consecutively but with a sufficient sampling frequency to provide comparable movement profiles for each point is to be understood in this context as a simultaneous measurement. A sufficient sampling frequency for this purpose is on the order of 1 to 10,000 Hz, such as, e.g., 1–100 Hz, including 2–25 Hz, such as 2–10 Hz.

In a preferred embodiment of the invention, the method for determining breathing patterns prescribes that the movement of the plurality of points be measured by the change in the distance from each point of the plurality of points to one or more reference points. This may be accomplished by any means for measuring distances known to the person skilled in the art. Preferably, this is done It is a significant feature of the method according to the invention, that the movement is measured over a time period so as to determine a breathing pattern. The minimum length of the time period is determined by the frequency and regularity of the breathing of the subject and the need for obtaining a statistically reliable breathing pattern. For the frequency breathing pattern parameter, the time period needs to encompass more than one breath (inspiration and expiration), preferably at least 3, such as at least 5, including at least 5 to 10. In particular embodiments the time period is in the range of half a minute to one minute or a few minutes. However, it should be noted that the above described time period is a recommended time to obtain a breathing pattern, the method can be used as well for extended time periods, e.g., to monitor eventual change in the breathing pattern. Such extended time periods may be on the order of several minutes up to many hours, such as 0.5 to 1 hours or longer, including 12 to 24 hours or longer.

Consequently, it is a highly advantageous feature of the method of the invention that a breathing pattern analysis may be obtained in a single acquisition, i.e. the movement of all points on which the analysis is based, is measured in the same acquisition, unlike e.g. prior art methods using the Elite system discussed above.

In a preferred embodiment of the invention the plurality of points on the body of a human subject comprises one or more points on each side of the sternum, more preferably the plurality of points is symmetrically distributed with respect to the sternum. It is to be understood that 'on each side of the sternum' refers to each side of the body divided by the plane that may be defined by the sternum and spine.

According to the method of the invention, the breathing pattern to be determined may be defined by various parameters that sufficiently will describe the breathing pattern for any given study or application. In preferred embodiments of the invention, the breathing patterns determined are defined by at least one or more of the breathing pattern parameters as described above but more preferably by all of them.

It is a particularly useful feature of a preferred embodiment of the invention to obtain a symmetry breathing pattern parameter. To obtain a symmetry breathing parameter the movement of a minimum of two points, one point on each side of sternum, needs to be measured.

In a preferred embodiment of the invention, a computer system receives the movement measurement data obtained by the method of the invention and calculates selected breathing pattern parameters.

As mentioned, the invention provides in another aspect a method for evaluating the effect of a medical condition on breathing functions by determining breathing patterns with the method of the invention. Such an evaluation may be useful for any condition that is suspected to have any effect on the breathing functions and may be used to monitor progression or regression of such a condition, e.g., to asses recovery of or the effect of treatment on subjects suffering from the condition. Such conditions include orthopedic diseases; diseases of the breathing organs including emphysema, respiratory insufficiency, and asthma; post-operative conditions including conditions after operations of organs in the chest and/or abdomen such as lung operations, coronary bypass operations, operations of the digestion system; post-injury conditions; conditions due to sleeping disorders such as sleep apnea; and rheumatism conditions.

In a preferred embodiment of the invention, the effect evaluated is one that has or may have an asymmetrical effect on breathing functions, such as e.g. a post-operative condition after a chest operation.

In certain useful embodiments of the invention, the breathing patterns determined by the invention are further correlated with other physical and/or chemical functions of a human body by a simultaneous measurement selected from the group comprising: electroencephalographic measurements, electrocardiographic measurements, electromyographic measurements, nerve conduction measurements, heart rate measurements, blood pressure measurements, measurements with a pulse oxymeter, and sound measurements such as, e.g., snoring. All of the said other measurements can provide digital output signals that may easily be correlated in time with the measured breathing patterns.

In a further aspect of the invention, an apparatus is provided for determining breathing patterns by the methods disclosed, said apparatus comprising an imaging device comprising one or more distance measurement devices that measure the change in distance from each point of the plurality of points to one or more reference points, for measuring the simultaneous movement of a plurality of points of a human body.

The apparatus is able to obtain data for a breathing pattern analysis in a single acquisition with the method of the invention, which is highly beneficial for obtaining high accuracy and precision of data, and to minimize inconvenience to measured subjects.

Preferably, the apparatus according to the invention measures the simultaneous movement of a plurality of points symmetrically distributed with respect to the sternum.

The apparatus according to the invention determines breathing patterns by a selected set of breathing pattern parameters, preferably such as those described above.

In a useful embodiment, the apparatus further comprises a computer system that utilizes the output signals from said imaging device for calculating breathing pattern parameters. Such a computer system is able to present the breathing pattern parameters on an output device such as a screen and/or a printer.

A further useful embodiment of the invention comprises a synchronized connection to one or more medical measurement means such as an electroencephalographic recording device, an electrocardiographic recording device, an electromyographic recording device, sonographic recording device, a nerve conduction measurement device, a heart rate meter, a pulse oxymeter, a blood pressure meter and a microphone. Said means can all provide digital output data that may be correlated in time with breathing patterns determined by the invention, thus providing useful methods for monitoring human subjects whether it is to evaluate a certain medical or physical condition (e.g. sleep).

An imaging device for use according to the invention may be any imaging device found to be practical for the purpose and known to the person skilled in the art and able to obtain data for determining the position and/or the movement of selected points with a sufficient precision.

In one embodiment, such an imaging device comprises a plurality of distance measurement devices held on a frame such that they are spatially and directionally adjustable. Such distance measurement devices are commercially available based on different physical interactions and include ultrasonic distance measurement sensors and optical distance sensors based on reflected light.

In a preferred embodiment, the apparatus according to the invention measures the absolute movement in space of the plurality of points, however, useful and reliable data may be obtained by measurement of movement in a particular direction such as the anterior-posterior direction which is the dominating direction of movement for the frontal area of the chest and abdomen.

In another embodiment, the imaging device of the apparatus comprises one or more cameras such as a CCD video camera, providing one or more images of the plurality of points on the body of the subject, and of one or more fixed reference points, said apparatus further comprising a computer system that calculates the distance from each point of the plurality of points to one or more of the said one or more reference points and thereby determines the movement of the plurality of points.

A further aspect of the invention relates to a method for determining breathing patterns, the method comprising:

a) providing a set of data for breathing movement measurements over a period of time;

b) entering the data into a computer;

c) calculating with a computer program breathing pattern parameters selected from the group comprising type of breathing, rhythm of breathing, magnitude of breathing movements, frequency of breathing movements, and symmetry of breathing movements.

The said set of data can be obtained by any of the methods described above. The data should be of sufficient sampling frequency to provide reliable and comparable, simultaneous movement profiles as described above. A computer program is used to calculate breathing pattern parameters such as those described above. Preferably all of the above-described parameters are calculated and used to determine breathing patterns.

Breathing pattern parameters may be calculated in the following way:

For each point the direction of movement is determined as the direction between the 'minimum' and 'maximum' point in the cyclical movement of each point during breathing. Optionally, a pre-determined direction is selected, such as the anterior-posterior direction. For each point, a movement vs. time function is determined with time on the x-axis and the movement along the movement direction or the pre-selected direction on the y-axis. Inspiration time is the time from a minimum to a maximum point and expiration time is the time from a maximum to a minimum point. The magnitude of breathing for each point is thus the difference between a maximum and minimum point with respect to the y-axis. Frequency of breathing may thus be calculated as the number of maximum points in a given time such as per minute, though one can also calculate the number of breathing cycles including partial breathing cycles, (e.g. if the measurement starts just before an inspiration and ends before an expiration) and rhythm of breathing is the average ratio between inspiration and expiration time.

To be able to calculate the 'type of breathing' parameter, points need to be selected at least at three heights of the body such that there is one point at the upper part of the ribs to determine 'high-costal' breathing, one point at the lower part of the ribs to determine 'low-costal' breathing, and one point at the abdomen to determine abdominal breathing. To determine a 'symmetry of breathing' parameter at least one point on each side of sternum needs to be selected as described above. A 'symmetry of breathing' parameter can then calculated simply as the difference in the magnitude of breathing for these two points.

EXAMPLES

Example 1

BMM Apparatus with Six Distance Measurement Devices

The apparatus comprises six ultrasonic distance sensors (Ultrasensor™, Ultra-U rev. B, Senix Corp. VT, USA), these are held by clamps on a frame comprising a larger angled arm and two smaller arms mounted on the larger arm. Each smaller arm bears three sensors that can be adjusted, both by moving the clamps along the arm and adjusting the angle of the sensor with respect to the arm, in such a way the sensors may be directed to selected points. The larger arm is mounted on table can be rotated such that the sensors are placed directly above a human subject lying on a bench, symmetrically with respect to the sternum of the subject, three sensors on each side of the sternum. The smaller arms can be rotated on the larger arm from a horizontal position to a vertical position in order to measure a subject in a lying to sitting position and in any inclination in-between.

A signal relay box receives signals from the sensors and forwards to a personal computer. The personal computer is programmed to calculate breathing pattern parameters with the signals received from the signal relay box.

Example 2

Measurement of Breathing Movements with BMM Apparatus

The apparatus from Example 1 was used to obtain breathing patterns for a human subject. The subject was laid down on a bench to a horizontal position. The larger arm of the BMM apparatus is turned such that that the two smaller arms are above and diagonal with the body of subject. The sensors are adjusted such that three sensors are directed to each side of the sternum, to points on a straight line diagonal with the body of the subject from the centerpoint of the collar bone (the centerpoint between articulatio sternoclavicularis and articulatio acromioclavicularis). The position of the points on the line is by the fourth rib, at the bottom rib, and at the height of the navel. Half-spheres of styrofoam are attached to the surface of the body of the subject, at the points that the sensors are directed at to give a better defined point of measurement for the interacting beam from the sensor.

Example 3

Breathing Pattern Determined for a Human Subject

A 30 years old male subject with no history of medical conditions affecting the breathing functions was subjected to breathing pattern analysis with the method of measurement as described in the Example 2. Measurements were recorded for 30 sec. for resting breathing and 59 sec. for maximum capacity breathing. The following breathing pattern parameters were determined for each measurement:

TABLE 1

|  |  | Abdominal | | Upper costal | | Lower costal | |
| --- | --- | --- | --- | --- | --- | --- | --- |
|  |  | left | right | left | right | left | right |
| resting | magnitude [mm] | 14.4 ± 2.4 | 14.4 ± 2.4 | 3.0 ± 0.5 | 2.5 ± 0.2 | 4.0 ± 0.4 | 4.0 ± 0.3 |
|  | frequency [min$^{-1}$] | 16.7 | 16.7 | 16.7 | 16.7 | 16.7 | 16.7 |
|  | rhythm | 1/0.83 | 1/0.83 | 1/0.83 | 1/0.83 | 1/0.83 | 1/0.83 |
|  | symmetry | 0.0 | | 0.5 | | 0.0 | |
| deep capacity | magnitude [mm] | 37.2 ± 0.4 | 39.3 ± 0.2 | 17.3 ± 1.7 | 17.6 ± 1.0 | 13.0 ± 0.5 | 15.6 ± 0.3 |
|  | frequency [min$^{-1}$] | 8.7 | 8.7 | 8.7 | 8.7 | 8.7 | 8.7 |
|  | rhythm | 1/0.92 | 1/0.92 | 1/0.92 | 1/0.92 | 1/0.92 | 1/0.92 |
|  | symmetry | | 2.1 | 2.6 | | 1.0 | |

Example 4

Average Breathing Patterns Determined for Healthy Subjects

The breathing pattern of 100 healthy individuals, 50 men and 50 women, were determined to obtain average values for breathing pattern parameters. The results are shown in table 2, divided by age and sex. Each group represents 10 individuals. 'Type' indicates the height points with greatest movement, 'RA' represents average range (magnitude) of both abdominal points, 'RLC' and 'RUC' are corresponding values for lower costal and upper costal measurements, frequency represents number of breathing cycles per minute. A '+' sign in the symmetry column represent symmetric breathing.

TABLE 2a resting breathing

| Type | | RA | RLC | RUC | Rhythm | Freq. | Symmetry |
| --- | --- | --- | --- | --- | --- | --- | --- |
| Women | | | | | | | |
| All | Abdominal | 6.49 | 3.87 | 3.38 | 100/90 | 14.0 | + |
| 20–29 | Abdominal | 4.95 | 3.94 | 4.02 | 100/104 | 14.0 | + |
| 30–39 | Abdominal | 7.06 | 3.67 | 3.07 | 100/80 | 12.6 | + |
| 40–49 | Abdominal | 7.26 | 4.03 | 4.11 | 100/96 | 13.9 | + |
| 50–59 | Abdominal | 8.22 | 3.43 | 3.01 | 100/91 | 14.1 | + |
| 60–69 | Abdominal | 7.66 | 4.19 | 2.53 | 100/78 | 15.4 | + |
| Men | | | | | | | |
| All | Abdominal | 7.47 | 3.35 | 2.64 | 100/84 | 14.0 | + |
| 20–29 | Abdominal | 5.01 | 2.92 | 2.73 | 100/98 | 14.0 | + |
| 30–39 | Abdominal | 7.31 | 3.23 | 3.10 | 100/92 | 12.6 | + |
| 40–49 | Abdominal | 8.71 | 4.42 | 3.21 | 100/75 | 13.9 | + |
| 50–59 | Abdominal | 8.74 | 3.24 | 2.36 | 100/81 | 14.1 | + |
| 60–89 | Abdominal | 7.34 | 3.10 | 2.04 | 100/73 | 15.4 | + |

TABLE 2b deep breathing

| Type | | RA | RLC | RUC | Rhythm | Freq. | Symmetry |
| --- | --- | --- | --- | --- | --- | --- | --- |
| Women | | | | | | | |
| All | UC | 17.52 | 16.01 | 18.04 | 100/84 | 7.3 | + |
| 20–29 | UC | 13.94 | 18.08 | 19.93 | 100/98 | 7.7 | + |
| 30–39 | Abd | 20.66 | 16.38 | 19.62 | 100/92 | 7.0 | + |
| 40–49 | UC | 17.52 | 16.38 | 19.62 | 100/75 | 7.0 | + |
| 50–59 | Abd | 20.59 | 17.03 | 18.23 | 100/81 | 8.0 | + |
| 60–69 | Equal | 15.05 | 16.05 | 16.84 | 100/73 | 7.0 | + |

TABLE 2b-continued deep breathing

| Type | | RA | RLC | RUC | Rhythm | Freq. | Symmetry |
| --- | --- | --- | --- | --- | --- | --- | --- |
| Men | | | | | | | |
| All | Abdominal | 24.68 | 19.72 | 18.37 | 100/82 | 7.4 | + |
| 20–29 | Abdominal | 26.65 | 24.01 | 21.75 | 100/75 | 6.6 | + |
| 30–39 | Abdominal | 23.12 | 14.25 | 17.25 | 100/84 | 7.0 | + |
| 40–49 | Abdominal | 23.53 | 19.07 | 16.79 | 100/89 | 8.8 | + |
| 50–59 | Abdominal | 26.09 | 18.81 | 19.72 | 100/80 | 7.3 | + |
| 60–69 | Abdominal | 23.61 | 22.47 | 16.11 | 100/84 | 7.3 | + |

What is claimed is:

1. A method for measuring breathing movements comprising:

measuring the simultaneous movement of a plurality of points of a human body, wherein the movement is measured by the change in the distance from each point of the plurality of points to one or more reference points;

providing a set of data for breathing movement measurements over a time period;

calculating breathing pattern parameters comprising: type of breathing, rhythm of breathing, magnitude of breathing movements, frequency of breathing movements, and symmetry of breathing movements, where type of breathing indicates whether the breathing movements are predominantly abdominal, low-costal or high-costal; and determining a breathing pattern based on the breathing pattern parameters.

2. The method according to claim 1, wherein a breathing pattern analysis is obtained for a subject in a single acquisition.

3. The method according to claim 1, wherein the plurality of points comprises one or more points on each side of the sternum.

4. The method according to claim 1, wherein the plurality of points is symmetrically distributed with respect to the sternum.

5. The method according to claim 1, wherein a computer system receives movement measurement data and calculates the breathing pattern parameters.

6. The method according to claim 1, further comprising correlating breathing patterns with other physical and/or chemical functions of a human body by a simultaneous measurement selected from the group comprising: electroencephalographic measurements, electrocardiographic measurements, electromyographic measurements, sonographic measurements, heart rate measurements, measurements with a pulse oxymeter, blood pressure measurements, and sound measurement such as for snoring.

7. A method for evaluating the effect of a medical condition on breathing functions by measuring breathing patterns according to any one of claims 1 to 6.

8. The method according to claim 7, wherein the medical condition is selected from the group comprising diseases of the breathing organs including emphysema, respiratory insufficiency, and asthma; post-operative conditions including conditions after operations of organs in the chest and/or abdomen such as lung operations, coronary bypass operations, operations of the digestion system; post-injury conditions; and rheumatism conditions.

9. The method according to claim 8, wherein the effect evaluated is an asymmetrical effect on breathing functions.

10. An apparatus for determining breathing patterns of a human comprising:

an imaging device comprising:

one or more distance measurement devices that measure the change in distance from each point of a plurality of points to one or more reference points;

wherein the apparatus measures the simultaneous movement of a plurality of points of a human body to calculate breathing pattern parameters comprising: type of breathing, rhythm of breathing, magnitude of breathing movements, frequency of breathing movements, and symmetry of breathing movements, where type of breathing indicates whether the breathing movements are predominantly abdominal, low-costal or high-costal; and wherein the apparatus determines a breathing pattern based on the breathing pattern parameters.

11. The apparatus according to claim 10, wherein the apparatus can obtain data for a breathing pattern analysis in a single acquisition.

12. The apparatus according to claim 10, wherein the apparatus measures the simultaneous movement of a plurality of points symmetrically distributed with respect to the sternum.

13. The apparatus according to claim 10, further comprising a computer system that utilizes the output signals from said imaging device for calculating breathing pattern parameters.

14. The apparatus according to claim 10, further comprising a synchronized connection to one or more medical measurement means selected from the group comprising: an electroencephalographic recording device, electrocardiographic recording device, electromyographic recording device, nerve conduction measurement device, sonographic recording device, heart rate meter, blood pressure meter and microphone.

15. The apparatus according to claim 13, wherein the computer system presents the breathing pattern parameters on an output device such as a screen and/or a printer.

16. The apparatus according to claim 10, wherein the imaging device comprises a plurality of distance measurement devices held on a frame such that they are spatially and directionally adjustable.

17. The apparatus according to claim 10, wherein anterior-posterior breathing movements are measured for each point of the plurality of points.

18. The apparatus according to claim 10, wherein the imaging device is an optical imaging device such as one or more cameras, providing an image of the plurality of points on a human body and one or more fixed reference points, the apparatus further comprising a computer system that calculates the distance from each point of the plurality of points to one or more of the said one or more reference points.

19. A method for determining breathing patterns comprising:

a) providing a set of data for breathing movement measurements over a period of time;

b) entering the data into a computer;

c) calculating with a computer program breathing pattern parameters selected from the group comprising type of breathing, rhythm of breathing, magnitude of breathing movements, frequency of breathing movements, and symmetry of breathing movements.

20. A method for determining breathing patterns comprising:

a) providing a set of data for breathing movement measurements over a period of time;

b) entering the data into a computer;

c) calculating with a computer program breathing pattern parameters comprising at least the following parameters: type of breathing, rhythm of breathing, magnitude of breathing movements, frequency of breathing movements, and symmetry of breathing movements.

* * * * *